United States Patent
Algawi et al.

(10) Patent No.: US 11,730,882 B2
(45) Date of Patent: Aug. 22, 2023

(54) DUAL-ACTION IRRIGATION PUMP WITH VARIABLE SPEED TO PROVIDE CONSTANT FLUID FLOW

(71) Applicant: Biosense Webster (Israel) Ltd., Yokneam (IL)

(72) Inventors: Yehuda Algawi, Binyamina (IL); Assaf Govari, Haifa (IL); Andres Claudio Altmann, Haifa (IL)

(73) Assignee: BIOSENSE WEBSTER (ISRAEL) LTD., Yokneam (IL)

( * ) Notice: Subject to any disclaimer, the term of this patent is extended or adjusted under 35 U.S.C. 154(b) by 54 days.

(21) Appl. No.: 16/586,377

(22) Filed: Sep. 27, 2019

(65) Prior Publication Data

US 2020/0206409 A1    Jul. 2, 2020

Related U.S. Application Data (60) Provisional application No. 62/786,404, filed on Dec. 29, 2018.

(51) Int. Cl.
*A61M 5/142* (2006.01)
*A61M 3/02* (2006.01)

(52) U.S. Cl.
CPC ........ *A61M 5/1422* (2013.01); *A61M 3/0202* (2021.05); *A61M 3/0258* (2013.01);
(Continued)

(58) Field of Classification Search
CPC .... A61M 60/122; A61M 60/40; A61M 60/50; A61M 5/1452; A61M 5/14216;
(Continued)

(56) References Cited

U.S. PATENT DOCUMENTS 4,065,230 A  * 12/1977 Gezari ................ A61M 5/1422
                                                    417/317
5,066,282 A     11/1991 Wijay et al.
(Continued)

FOREIGN PATENT DOCUMENTS

CN      103153839 A     6/2013
CN      105188803 A     12/2015
(Continued)

OTHER PUBLICATIONS

European Search Report for Application No. EP 19220175.4, dated Apr. 17, 2020, 9 pages.
(Continued)

*Primary Examiner* — Scott J Medway
(74) *Attorney, Agent, or Firm* — Lewis Roca Rothgerber Christie LLP (57) ABSTRACT

A dual-action pump includes a cylinder, a piston and a controller. The cylinder includes first and second inlet-outlet ports, each of the first and second inlet-outlet ports is configured to alternately intake a fluid to the cylinder and output the fluid from the cylinder. The piston is configured to be moved within the cylinder in a periodic cycle that alternately reverses a direction of movement of the piston, so as to pump the fluid through the first and second inlet-outlet ports. The controller is configured to control the movement of the piston within the cylinder, including setting to the piston: (a) a first speed, during a first predefined interval that precedes reversing the direction of movement, (b) a second speed, larger than the first speed, during a second predefined interval that follows reversing the direction, and (c) a baseline speed, smaller than the first speed, outside the first and second intervals.

20 Claims, 4 Drawing Sheets

(52) U.S. Cl.
CPC .............. *A61M 2205/3334* (2013.01); *A61M 2205/3337* (2013.01); *A61M 2210/125* (2013.01)

(58) Field of Classification Search
CPC .............. A61M 5/1422; A61B 18/1492; A61B 2218/002; A61B 2018/00011
See application file for complete search history.

(56) References Cited

U.S. PATENT DOCUMENTS

| | | | |
|---|---|---|---|
| 5,089,017 A * | 2/1992 | Young | A61M 60/40 623/3.11 |
| 5,092,037 A * | 3/1992 | Pinkerton | F04B 7/06 29/428 |
| 5,322,418 A * | 6/1994 | Comer | A01C 23/028 111/127 |
| 5,391,199 A | 2/1995 | Ben-Haim | |
| 6,239,724 B1 | 5/2001 | Doron et al. | |
| 6,332,089 B1 | 12/2001 | Acker et al. | |
| 6,484,118 B1 | 11/2002 | Govari | |
| 6,618,612 B1 | 9/2003 | Acker et al. | |
| 6,690,963 B2 | 2/2004 | Ben-Haim et al. | |
| 6,827,701 B2 | 12/2004 | MacMahon et al. | |
| 6,913,933 B2 | 7/2005 | Jacobs et al. | |
| 9,622,814 B2 | 4/2017 | Wang et al. | |
| 2002/0065455 A1 | 5/2002 | Ben-Haim et al. | |
| 2002/0198496 A1 * | 12/2002 | Duchon | A61M 5/16827 604/154 |
| 2003/0018252 A1 * | 1/2003 | Duchon | A61B 6/481 600/432 |
| 2003/0120150 A1 | 6/2003 | Govari | |
| 2004/0068178 A1 | 4/2004 | Govari | |
| 2011/0152683 A1 * | 6/2011 | Gerrans | A61B 5/6853 600/435 |
| 2012/0108899 A1 * | 5/2012 | Da Cruz | A61M 5/1452 600/106 |
| 2015/0073346 A1 | 3/2015 | Visconti et al. | |
| 2016/0317741 A1 * | 11/2016 | List | A61M 5/1413 |
| 2018/0014878 A1 * | 1/2018 | Govari | F04B 43/02 |
| 2018/0272108 A1 * | 9/2018 | Padilla | A61B 5/6857 |

FOREIGN PATENT DOCUMENTS

| | | | |
|---|---|---|---|
| WO | WO 96/05768 A1 | 2/1996 | |
| WO | WO-2016033351 A2 * | 3/2016 | .......... A61M 5/1422 |

OTHER PUBLICATIONS

Chinese First Office Action for Application No. CN 201911390113.6, dated Jan. 28, 2023, 4 pages and translation of text, 7 pages.
Chinese Search Report for Application No. CN201911390113.6, 3 pages.

* cited by examiner

DUAL-ACTION IRRIGATION PUMP WITH VARIABLE SPEED TO PROVIDE CONSTANT FLUID FLOW

CROSS-REFERENCE TO RELATED APPLICATIONS

This application claims the benefit of U.S. Provisional Patent Application 62/786,404, filed Dec. 29, 2018. This application is related to a U.S. Patent Application entitled "Irrigation Pump with Ablation and Non-Ablation Operational Modes," U.S. patent application Ser. No. 16/586,421, filed Sep. 27, 2019, each of the prior applications is hereby incorporated by reference as if set forth in full herein this application.

FIELD OF THE INVENTION

The present invention relates generally to pumps, and particularly to medical irrigation pumps.

BACKGROUND OF THE INVENTION

Irrigation pumps are used in some medical procedures. Various techniques have been developed for improving performance of medical irrigation pumps.

For example, U.S. Pat. No. 6,913,933 describes a method for improving the fluid dispense rate in a metering system utilizing speed includes the steps of modifying the fluid flow rate profile during a portion thereof so as substantially increase or decrease the speed of the motor during certain portions of a metering cycle in order to improve the efficiency of the metering system.

U.S. Pat. No. 5,066,282 describes a disposable, positive-displacement piston pump, having a polycarbonate body, a piston, an inlet valve, and an outlet valve. The outlet valve is connected to an exit chamber, which is separated from the exit valve by an elastomeric membrane. The elastomeric membrane encloses an accumulation chamber which is filled with a fluid such as air under atmospheric pressure. Pulsations in outlet pressure caused by stroking of the piston are dampened by the flexing action of the elastomeric membrane, compressing the fluid within the accumulator chamber.

U.S. Pat. No. 9,622,814 describes an ablation catheter which controls the temperature and reduces the coagulation of biological fluids on an electrode of a catheter, prevents the impedance rise of tissue in contact with the electrode, and maximizes the potential energy transfer to the tissue, thereby allowing an increase in the lesion size produced by the ablation. The electrode includes passages positioned to allow saline flow out of an inner cavity of the electrode. This fluid flow is pulsatile to increase turbulence, reducing areas of stagnant flow, and produces a desired cooling effect.

SUMMARY OF THE INVENTION

An embodiment of the present invention that is described herein provides a dual-action pump including a cylinder, a piston and a controller. The cylinder includes first and second inlet-outlet ports, each of the first and second inlet-outlet ports is configured to alternately intake a fluid to the cylinder and output the fluid from the cylinder. The piston is configured to be moved within the cylinder in a periodic cycle that alternately reverses a direction of movement of the piston, so as to pump the fluid through the first and second inlet-outlet ports. The controller is configured to control the movement of the piston within the cylinder, including setting to the piston: (a) a first speed, during a first predefined interval that precedes reversing the direction of movement, (b) a second speed, larger than the first speed, during a second predefined interval that follows reversing the direction, and (c) a baseline speed, smaller than the first speed, outside the first and second intervals.

In some embodiments, the dual-action pump includes a piston position sensing assembly (PPSA), which is configured to produce a control signal indicative of a position of the piston within the cylinder, the controller is configured to receive the control signal, and to control the movement of the piston based on the control signal. In other embodiments, the controller is configured to control the movement of the piston between first and second ends of the cylinder, the PPSA includes (a) a first electrical switch configured to produce a first position signal when the piston is situated within a predefined distance from the first end, and (b) a second electrical switch configured to produce a second position signal when the piston is situated within a predefined distance from the second end, and the PPSA is configured to produce the control signal based on at least one of the first and second position signals.

In an embodiment, the controller is configured to control a given volume of the fluid to be pumped through the first and second inlet-outlet ports during a first time period including at least the first and second predefined distance intervals, and to control the same given volume of the fluid to be pumped through the first and second inlet-outlet ports during a second time period that is approximately equal to the first time period, when the piston is outside the first and second distance intervals. In another embodiment, at least one of the first and second inlet-outlet ports is coupled to a fluid reservoir via a first pipe, and to a catheter via a second pipe, so as to irrigate tissue with the fluid during a medical procedure.

There is additionally provided, in accordance with an embodiment of the present invention, a method for pumping a fluid in a medical procedure, the method includes, in a dual-action pump including a cylinder having first and second inlet-outlet ports for alternately in-taking a fluid to the cylinder and outputting the fluid from the cylinder by each of the first and second inlet-outlet ports, moving a piston within the cylinder in a periodic cycle that alternately reverses a direction of movement of the piston so as to pump the fluid through the first and second inlet-outlet ports. The movement of the piston within the cylinder is controlled, including setting to the piston: (a) a first speed, during a first predefined interval that precedes reversing the direction of movement, (b) a second speed, larger than the first speed, during a second predefined interval that follows reversing the direction, and (c) a baseline speed, smaller than the first speed, outside the first and second intervals.

There is further provided, in accordance with an embodiment of the present invention, a dual-action pump that includes a cylinder, a piston and a controller. The cylinder has first and second ends and includes first and second inlet-outlet ports, each of the first and second inlet-outlet ports is configured to alternately intake a fluid to the cylinder and output the fluid from the cylinder. The piston is configured to be moved within the cylinder between the first and second ends by alternately reversing a direction of movement of the piston, so as to pump the fluid through the first and second inlet-outlet ports. The controller is configured to control the movement of the piston within the cylinder, including: (a) choosing between first and second operational modes, (b) in the first operational mode, controlling the piston to oscillate over a predefined distance interval that does not exceed a predefined distance from the first end or from the second end, and (c) in the second operational mode, controlling the piston to move at a selected speed between the first end and the second end.

In some embodiments, the controller is configured to receive a signal indicative of a position of the piston within the cylinder, and to control the movement of the piston based on the signal. In other embodiments, at least one of the first and second inlet-outlet ports is coupled to a fluid reservoir via a first pipe, and to a catheter via a second pipe, so as to irrigate tissue with the fluid during a medical procedure. In yet other embodiments, the medical procedure includes tissue ablation by the catheter, and the controller is configured to choose the second operational mode in response to receiving a control signal indicative of the tissue ablation.

In an embodiment, the tissue ablation includes positioning the catheter at first and second ablation sites, and, in the second operational mode, the controller is configured to control the piston to: (a) move at a first selected speed when the catheter is positioned at the first ablation site, and (b) move at a second, different, selected speed when the catheter is positioned at the second ablation site. In another embodiment, in the second operational mode, the controller is configured to control the piston to move at a constant speed. In yet another embodiment, in the second operational mode, the controller is configured to control the piston to move at a variable speed.

There is additionally provided, in accordance with an embodiment of the present invention, a method for pumping a fluid in a medical procedure, the method includes in a dual-action pump including a cylinder having first and second ends and including first and second inlet-outlet ports for alternately in-taking a fluid to the cylinder and outputting the fluid from the cylinder by each of the first and second inlet-outlet ports, moving a piston within the cylinder between the first and second ends by alternately reversing a direction of movement of the piston, so as to pump the fluid through the first and second inlet-outlet ports. The movement of the piston within the cylinder, including: (a) choosing between first and second operational modes, (b) in the first operational mode, controlling the piston to oscillate over a predefined interval that does not exceed a predefined distance from the first end or from the second end, and (c) in the second operational mode, controlling the piston to move at a selected speed between the first end and the second end.

There is further provided, in accordance with an embodiment of the present invention, a dual-action pump that includes a cylinder, a piston and a controller. The cylinder has first and second ends and including first and second inlet-outlet ports, each of the first and second inlet-outlet ports is configured to alternately intake a fluid to the cylinder and output the fluid from the cylinder. The piston is configured to be moved within the cylinder between the first and second ends by alternately reversing a direction of movement of the piston, so as to pump the fluid through the first and second inlet-outlet ports. The controller is configured to control the movement of the piston within the cylinder, including: (a) choosing between first and second operational modes, (b) in the first operational mode, controlling the piston to remain stationary at a predefined distance larger than zero from the first end or from the second end, and (c) in the second operational mode, controlling the piston to move at a selected speed between the first end and the second end.

The present invention will be more fully understood from the following detailed description of the embodiments thereof, taken together with the drawings in which:

DETAILED DESCRIPTION OF EMBODIMENTS

Overview

Some cardiac procedures comprise tissue ablation, such as radio-frequency (RF) ablation, carried out at predefined sites of a patient heart for treating arrhythmia. An RF ablation system typically comprises ablation electrodes that are coupled to a distal end of a catheter, and a navigation subsystem, such as a magnetic position tracking subsystem, for navigating the catheter distal-end to the ablation sites. The RF ablation system further comprises an irrigation assembly for irrigating the ablated tissue with irrigation fluids. It is important to irrigate the tissue before and during ablation, using controlled irrigation parameters such as flow rates, without introducing electrical noise that may interfere with magnetic fields of the magnetic position tracking subsystem.

Embodiments of the present invention that are described hereinbelow provide methods and apparatus for improving control of irrigation parameters during ablation procedures. In some embodiments, an irrigation assembly comprises (a) a fluid reservoir containing the irrigation fluid, (b) one or more irrigation openings at a catheter distal-end, for irrigating tissue of a patient heart, and (c) a dual-action pump, which is configured to pump the irrigation fluid between the reservoir and irrigation openings.

In some embodiments, the dual-action pump comprises a cylinder having first and second ends, also referred to herein as walls, and comprising first and second inlet-outlet ports, each of which is coupled to the reservoir and the catheter. Each of the inlet-outlet ports is configured to alternately, intake the fluid from the reservoir to the cylinder and output the fluid from the cylinder to the catheter distal end. The dual-action pump comprises a piston, which is configured to be moved within the cylinder between the first and second walls by alternately reversing the direction of movement of the piston, so as to pump the fluid through the first and second inlet-outlet ports.

In some embodiments, the dual-action pump further comprises a controller, which is configured to control the movement of the piston within the cylinder. The controller is configured to choose between ablation and non-ablation operational modes of the dual-action pump. In the ablation operational mode, the controller is configured to control the piston to move at a selected speed between the first wall and the second wall, so as to irrigate the ablated site. In the non-ablation operational mode, the controller is configured to control the piston to oscillate over a predefined interval that does not exceed a predefined distance from the first wall or from the second wall of the cylinder, so as to maintain low irrigation flows between the tissue ablations. In some embodiments, the controller is configured to receive a signal indicative of the position of the piston within the cylinder, and to control the movement of the piston based on the signal. The controller is further configured to receive a control signal, and to choose between the non-ablation and ablation operational modes based on the control signal.

In other embodiments, the piston is configured to be moved between the walls, in a periodic cycle that alternately reverses a direction of movement of the piston at the walls, so as to pump the fluid through the first and second inlet-outlet ports. In such embodiments, the controller is configured to control the movement of the piston between the walls, including setting to the piston: (a) a first speed, during a first preset interval from the wall that precedes reversing the direction of movement, (b) a second speed, larger than the first speed, during a second preset interval from the wall that follows reversing the direction, and (c) a baseline speed, smaller than the first speed, outside the first and second preset intervals. The controller is configured to set the size of the first and second preset intervals and the corresponding first and second speeds, in order to control the flow rate of the irrigation fluid relative to the specified flow rate, and when applicable, to maintain a constant flow rate through the inlet-outlet ports when the piston reverses directions.

The disclosed techniques improve the patient safety and the quality of ablation procedures by improving control of the irrigation parameters during ablation and between ablations of the heart tissue.

System Description

Figure 1:
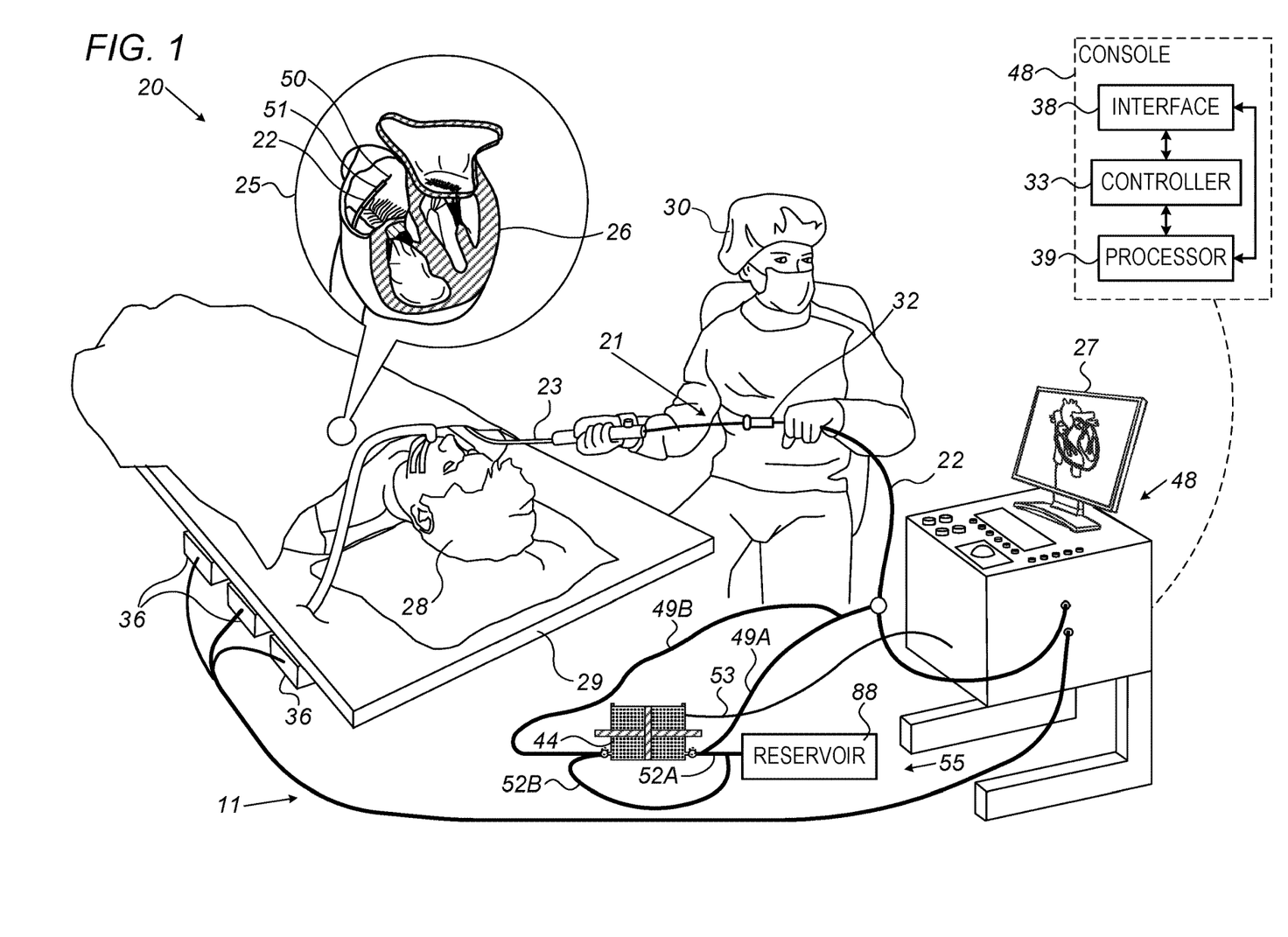
FIG. 1 is a schematic, pictorial illustration of a catheter-based ablation system, in accordance with an embodiment of the present invention.

FIG. 1 is a schematic, pictorial illustration of a catheter-based ablation system 20, in accordance with an embodiment of the present invention. System 20 comprises a catheter 21, having a shaft distal end 22 that is navigated by a physician 30 into a heart 26 of a patient 28 via the vascular system. In some embodiments, physician 30 inserts shaft distal end 22 through a sheath 23, while manipulating distal end 22 using a manipulator 32 located at the proximal end of catheter 21.

Reference is now made to an inset 25. In some embodiments, system 20 comprises a magnetic sensor 51, also referred to herein as a magnetic position tracking sensor, or sensor 51 for brevity, and an ablation catheter 50, which are coupled to distal end 22.

In the embodiments, catheter 21 may be used for various procedures, such as electrophysiological (EP) mapping of heart 26 and for ablating selected tissue of heart 26. Catheter 21 comprises irrigation openings for irrigating tissue of heart 26 during the EP procedure and in particular during ablation as will be described in detail below.

In some embodiments, the proximal end of catheter 21 is electrically connected to a control console 48 and, in parallel, to an irrigation assembly 11 that supplies irrigation fluid 88, also referred to herein as fluid 88 for brevity, for the ablation and other procedures carried out by system 20. In an embodiment, console 48 comprises a processor 39, a controller 33 and interface circuit 38, which is configured to exchange signals between processor 39 and/or controller 33, and various components, modules and assemblies of system 20, as will be described in detail below.

In some embodiments, interface circuits 38 are configured to receive electrical signals from catheter 21 and other sensors of system 20. Circuits 38 are further configured to send electrical signals, received from processor 39 and controller 33, to various components and assemblies of system 20, such as applying power via catheter 21 for ablating tissue of heart 26, and for controlling the other components and assemblies of system 20. For example, during ablation, catheter 21 is configured to irrigate the ablated tissue with irrigation fluid as will be described in detail below. In an embodiment, processor 39 is configured to control ablation electrodes (not shown), disposed at distal end 22, to apply radiofrequency (RF) energy to tissue of heart 26. As will be described in detail below, controller 33 is configured to apply irrigation fluid 88 to the tissue, e.g., during the ablation procedure.

In some embodiments, system 20 comprises multiple (e.g., three) magnetic field generators 36, configured to produce alternating magnetic fields. Field generators 36 are placed at known positions external to patient 28, for example, below a patient table 29.

In some embodiments, console 48 further comprises a display 27, and a driver circuit (not shown), which is configured to drive magnetic field generators 36.

During an EP procedure physician 30 navigates distal end 22 of catheter 21 in heart 26. In some embodiments, in response to the magnetic fields irradiated from field generators 36, magnetic sensor 51 is configured to produce a position signal, indicative of the position of distal end 22 in heart 26.

In some embodiments, based on the position signal received from sensor 51, processor 39 is configured to display, e.g., on display 27, the position of distal end 22 in the coordinate system of system 20.

This method of position sensing is implemented, for example, in the CARTO™ system, produced by Biosense Webster Inc. (Irvine, Calif.) and is described in detail in U.S. Pat. Nos. 5,391,199, 6,690,963, 6,484,118, 6,239,724, 6,618,612 and 6,332,089, in PCT Patent Publication WO 96/05768, and in U.S. Patent Application Publications 2002/0065455 A1, 2003/0120150 A1 and 2004/0068178 A1.

In some embodiments, irrigation assembly 11 comprises a pump 44, in the present example a dual-action irrigation pump whose structure and functionality are described, for example, in FIGS. 2, 3A and 5 below. Irrigation assembly further comprises a fluid reservoir 55, which is configured to contain irrigation fluid 88, such as a saline solution or any other type of fluid suitable for irrigating tissue of heart 26.

In some embodiments, irrigation assembly 11 comprises tubes 52A and 52B, configured to flow fluid 88 between reservoir 55 and pump 44. Irrigation assembly 11 further comprises tubes 49A and 49B, configured to flow fluid 88 between pump 44 and catheter 21.

In some embodiments, controller 33 is configured to receive, via a cable 53, electrical signals indicative of control parameters of irrigation assembly 11. Based on the control parameters, controller 33 is configured to control the flow of fluid 88 to distal end 22 and within irrigation assembly 11. Embodiments of method and apparatus for controlling the flow of fluid 88 are described in detail in FIGS. 2-6 below.

Processor 39 and/or controller 33 typically comprise a general-purpose processor or controller, which is programmed in software to carry out the functions described herein. The software may be downloaded to Processor 39 and controller 33 in electronic form, over a network, for example, or it may, alternatively or additionally, be provided and/or stored on non-transitory tangible media, such as magnetic, optical, or electronic memory.

Controlling Fluid Pumping in Dual-Action Pump

Figure 2:
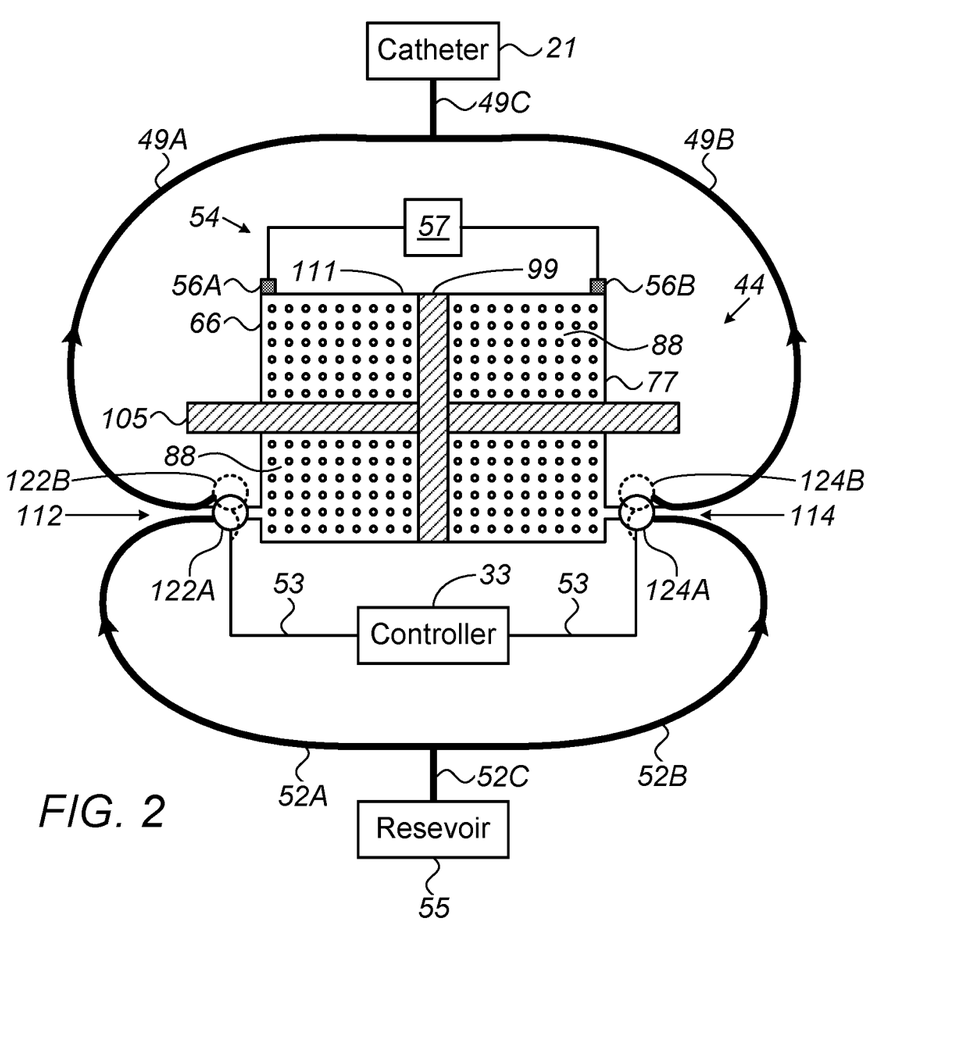
FIG. 2 is a schematic, side view of a dual-action irrigation pump of an ablation system, in accordance with an embodiment of the present invention.

FIG. 2 is a schematic, side view of pump 44, in accordance with an embodiment of the present invention. In some embodiments, pump 44 comprises a cylinder 111, which is configured to contain irrigation fluid 88 for irrigating tissue of heart 26. Pump 44 further comprises a piston 99, which is configured to be moved within cylinder 111, e.g., along a shaft 105, using a stepper motor (not shown), or any suitable type of motion apparatus, such as but not limited to any other type of suitable motor or actuator. In the example of pump 44, cylinder 111 and piston 99 have, both, a circular cross-section.

In the context of the present patent application and in the claims, the term "cylinder" refers, as a term of art, to any suitable container in which piston 99, or any other suitable type of piston, moves. In this context, the cylinder and the piston may have any suitable cross-section, not necessarily circular.

In some embodiments, cylinder 111 has a left wall 66 and a right wall 77, also referred to herein, respectively, as "first and second ends" of cylinder 111, or as "walls 66 and 77," for brevity. In some embodiments, cylinder 111 comprises inlet-outlet ports 112 and 114, formed in walls 66 and 77, respectively.

In the context of the present patent application and in the claims, the respective terms "inlet-outlet ports 112 and 114," "port 112 and 114," and "first and second inlet-outlet ports," are used interchangeably and refer to openings in cylinder 111. In an embodiment, each of the first and second inlet-outlet ports is configured to alternately, intake fluid 88 to cylinder 111 and output fluid 88 from cylinder 111.

In some embodiments, each of inlet-outlet ports 112 and 114 may have two openings. Note that in the side view of FIG. 2, both openings are in the same plane (which is orthogonal to the plane of FIG. 2), therefore the second opening is hidden behind the first opening and both openings are shown as a single opening. In some embodiments, the first opening of inlet-outlet port 112 is coupled, via a valve 122A, to tube 52A, and the second opening of inlet-outlet port 112 is coupled, via a valve 122B, to tube 49A. Similarly, the first opening of inlet-outlet port 114 is coupled, via a valve 124A, to tube 52B, and the second opening of inlet-outlet port 114 is coupled, via a valve 124B, to tube 49B.

In some embodiments, tubes 49A and 49B are coupled to a common tube 49C, which is also coupled to catheter 21. Similarly, tubes 52A and 52B are coupled to a common tube 52C, which is also coupled to reservoir 55.

In some embodiments, in a dual-action pump, such as pump 44, each of inlet-outlet ports 112 and 114 exchanges fluid 88 with two entities, in the present example, reservoir 55 and catheter 21. Each of valves 122A, 122B, 124A and 124B, is configured to enable the flow of fluid 88 in one direction and to block the flow of fluid 88 in the opposite direction, and also to reverse the flow direction. Controller 33 is configured to control the flow direction of fluid 88 by switching the movement direction of piston 99. In such embodiments, the movement of piston 99 determines the flow direction in the aforementioned valves. For example, when piston 99 is moved toward wall 77, valve 122A intakes fluid 88 from reservoir 55, via tubes 52C and 52A, into cylinder 111, and at the same time, valve 124B outputs fluid 88 from cylinder 111, via tubes 49B and 49C, into catheter 21. In alternative embodiments, controller 33 is configured to control, via cables 53, the flow direction of valves 122A, 122B, 124A and 124B.

In some embodiments, piston 99 is moved within cylinder 111 in a periodic cycle that alternately reverses the direction of movement of piston 99, so as to pump fluid 88 through inlet-outlet ports 112 and 114. For example, when piston 99 is moved in a reversed direction toward left wall 66, valve 122B enables outflow of fluid 88 that is disposed between piston 99 and wall 66 to flows from pump 44, via port 112 and tubes 49A and 49C, into catheter 21 for irrigating tissue of heart 26. At the same time, valve 124A enables flow of fluid 88 from reservoir 55, via tubes 52C and 52B and through port 114, into cylinder 111.

In some embodiments, pump 44 comprises a piston position sensing assembly (PPSA) 54, which is configured to sense the position of piston 99 along shaft 105, and to produce a signal indicative of the position of piston 99 within cylinder 111. In some embodiments, PPSA 54 comprises any suitable type of position sensor. In the example of FIG. 2, PPSA 54 comprises electrical switches 56A and 56B, disposed in close proximity to walls 66 and 77, respectively. In some embodiments, electrical switches 56A and 56B are electrically coupled to a controller 57 that is electrically connected to controller 33. In other embodiments, electrical switches 56A and 56B may be electrically coupled directly to controller 33.

In some embodiments, PPSA 54 may be calibrated during the assembly of system 20 and/or at least prior to the first medical procedure that requires irrigation. During the calibration, controller 33 controls the movement of piston along shaft 105, between walls 66 and 77. When piston reaches wall 66, electrical switch 56A sends to controller 57, a signal indicative of the position of piston 99. Subsequently, controller 33 controls the movement of piston 99, within cylinder 111, to wall 77, and count steps of the stepper motor. When piston 99 reaches wall 77, electrical switch 56B sends to controller 57, a signal indicative of the position of piston 99, and controller 57 concludes the calibration.

In some embodiments, based on the calibration, the counted number of steps and the direction thereof, controller 57 may send to controller 33 the aforementioned signal indicative of the position of piston 99 within cylinder 111.

In alternative embodiments, piston 99 may not make physical contact with walls 66 and 77, but approaches the walls, e.g., within a predefined distance of a few millimeters or any other suitable distance.

In other embodiments, PPSA 54 may have any other suitable configuration, using any suitable technique for producing the signals indicative of the current position of piston 99 within cylinder 111.

This particular configuration of irrigation assembly 11 and system 20 is shown by way of example, in order to illustrate certain problems that are addressed by embodiments of the present invention and to demonstrate the application of these embodiments in enhancing the performance of such a system. Embodiments of the present invention, however, are by no means limited to this specific sort of example system, and the principles described herein may similarly be applied to other sorts of medical ablation and/or irrigation systems.

Figure 3A:
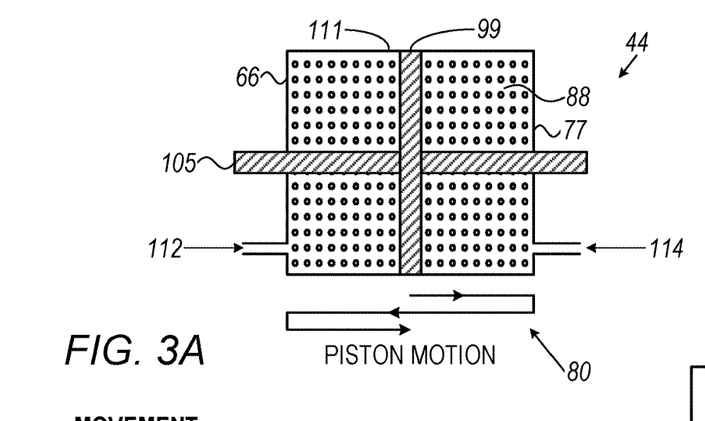
FIG. 3A is a schematic, pictorial illustration of a movement of a piston within a cylinder of a dual-action medical irrigation pump, in accordance with an embodiment of the present invention.

FIG. 3A is a schematic, pictorial illustration of a movement of piston 99 within cylinder 111 during irrigation, in accordance with an embodiment of the present invention. In some embodiments, controller 33 is configured to control the movement of piston 99 in a periodic cycle that alternately reverses the direction of movement of piston 99 using a movement profile 80, so as to pump fluid 88 at a constant rate.

Note that controller 33 has to change the movement direction when piston 99 reaches any of walls 66 and 77, therefore, piston 99 stands still (i.e., remains stationary) at walls 66 and 77 before changing direction. In other words, the movement speed of piston 99 when positioned at walls 66 and 77 is zero, and therefore, fluid 88 is not pumped at these positions. In an embodiment, controller 33 is configured to maintain the constant flow rate of fluid 88 using a technique described in FIG. 3B below.

In other embodiments, piston 99 does not make physical contact with at least one of walls 66 and 77. In such embodiments, controller 33 may change the movement direction before piston 99 reaches any of walls 66 and 77. For example, controller 33 may change the movement direction of piston 99 when piston 99 approaches wall 66 within a predetermined interval of a few millimeters, or within any other suitable predefined interval.

Controlling Constant Rate of Fluid Pumping Using Dual-Action Pump

Figure 3B:
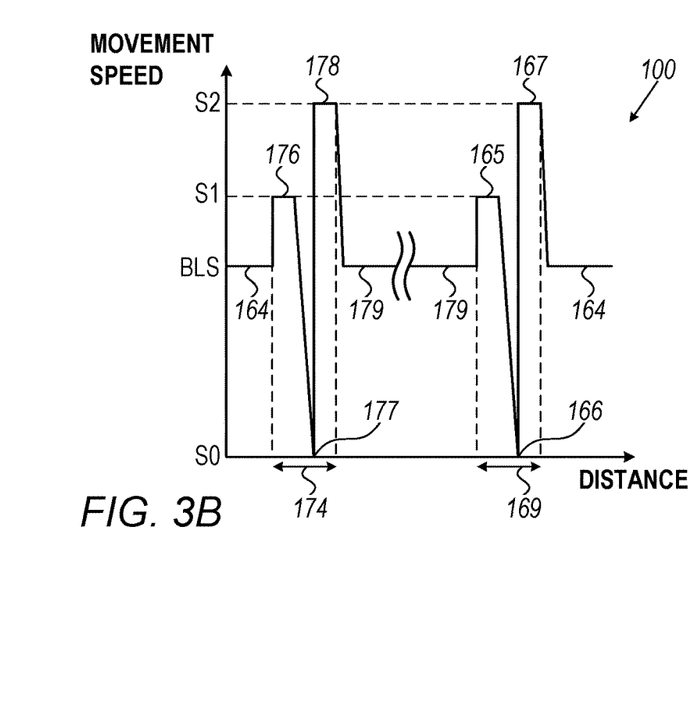
FIG. 3B is a graph that schematically illustrates a movement profile of a piston in a cylinder of a dual-action medical irrigation pump, in accordance with an embodiment of the present invention.

FIG. 3B is a graph 100 that schematically illustrates a movement profile of piston 99 within cylinder 111 during irrigation, in accordance with an embodiment of the present invention. In some embodiments, graph 100 shows the movement speed of piston 99 as a function of the position of piston 99 in accordance with movement profile 80 shown in FIG. 3A above. For the sake of conceptual clarity, graph 100 is divided into multiple section corresponding to the position of piston 99 within cylinder 111.

In some embodiments, when piston 99 is positioned at section 164, which is situated between walls 66 and 77 as shown in FIG. 3A, controller 33 is configured to move piston 99 toward wall 77 at a baseline speed, referred to as "BLS" on the movement speed axis of graph 100. Note that the BLS, depends the dimensions of cylinder 111 defining the volume of fluid 88, and also based on the predefined parameters of the ablation procedure, such as but not limited to the ablation power and the target temperature of the ablated tissue.

As described above, piston 99 is moved toward wall 77 and PPSA 54 sends signals indicative of the respective positions of piston 99 within cylinder 111. Note that controller 33 reverses the movement direction of piston 99 upon reaching walls 66 and 77, or in close proximity to the wall.

In some embodiments, when piston 99 is at a predefined interval 176 (e.g., about 1 mm or any other suitable interval) from wall 77, controller 33 receives from PPSA a signal indicative of the corresponding position thereof, and in response, controller 33 sets to piston a first speed, S1, which is larger than BLS.

In the context of the present disclosure and in the claims, the terms "about" or "approximately" for any numerical values or ranges indicate a suitable dimensional tolerance that allows the part or collection of components to function for its intended purpose as described herein. More specifically, "about" or "approximately" may refer to the range of values ±20% of the recited value, e.g. "about 90%" may refer to the range of values from 71% to 99%.

In some embodiments, when piston 99 is in close proximity (e.g. about 2 mm) to wall 77, controller may reduce the speed of piston 99 to a complete stop, shown as a speed "S0" at point 177, which corresponds to piston 99 having physical contact with wall 77, or is within a predetermined interval from wall 77.

In some embodiments, in response to receiving from PPSA 54 a signal indicating that piston 99 makes physical contact with wall 77 (or is within a predetermined interval therefrom), controller 33 is configured to reverse the movement direction of piston 99 toward wall 66, and to set to piston 99 a movement speed S2 shown at a predefined interval 178 of graph 100. Note that intervals 176 and 178 may overlap in position (e.g., both are in proximity to wall 77), but having piston moved in different directions, and therefore, are shown as different intervals in graph 100.

In some embodiments, controller 33 is configured to compensate for the reduced flow rate of pump 44 caused by the complete stop at wall 77 (corresponding to point 177), by setting to piston 99 speed S1 at interval 176 that precedes reversing the direction of movement, and speed S2 at interval 178 that follows reversing the direction of movement. As described above, speed S2 is larger than S1 and both speeds S1 and S2 are larger than BLS, this sequence results in a flow rate increase of pump 44 so as to compensate for the reduced flow rate when piston is situated in close proximity to, and is making contact with wall 77.

In such embodiments, at a first time interval referred to herein as a section 174 of graph 100, pump 44 flows (e.g., to catheter 21) at a given time, volume of fluid 88 similar to the volume flown by pump 44 if piston 99 were moved at the BLS speed. In other words, controller 33 sets pump 44 to retain constant flow of fluid 88 also when reversing the direction of movement at walls 66 and 77.

In some embodiments, controller 33 is configured to set speeds S1 and S2 and the physical dimensions of intervals 176 and 178 using any suitable arrangement that obtains the aforementioned constant flow of fluid 88 by pump 44. In such embodiments, controller 33 may set intervals 176 and 178 to have similar or different physical travel and/or duration relative to one another. For example, controller 33 may set speed S2 substantially larger than speed S1, and interval 178 shorter than interval 176, or may use any other suitable combination of speeds and interval durations for optimizing the flow rate of pump 44.

In some embodiments, in response to receiving from PPSA 54 a signal indicating that piston concluded the travel in interval 178, controller 33 controls the movement of piston 99 toward wall 66 at a predefined interval 179 situated outside intervals 176 and 178, and sets the speed of piston 99 to BLS.

In some embodiments, in response to receiving from PPSA 54 a signal indicating that piston concluded the travel in interval 179, controller 33 sets the speed of piston 99 to S1 at a predefined interval 165 that precedes reversing the direction of movement at wall 66.

Using the same sequence described above for point 177, in response to receiving from PPSA 54 a signal indicating that piston concluded the travel in interval 165, controller 33 reduces the moving speed of piston 99 to a complete stop at point 166, which corresponds to piston 99 having physical contact with wall 66 or is within a predetermined interval therefrom.

In some embodiments, in response to receiving from PPSA 54 a signal indicating that piston 99 makes physical contact with (or is within a predetermined interval from) wall 66, controller 33 is configured to reverse the movement direction of piston 99 toward wall 77, and to set to piston 99 movement speed S2 at a predefined interval 167 that follows reversing the direction of movement.

In some embodiments, in response to receiving from PPSA 54 a signal indicating that piston 99 has concluded travelling along interval 167, controller 33 controls the movement of piston 99 toward wall 77 at interval 164 situated outside intervals 165 and 167, and sets the speed of piston 99 to BLS.

In some embodiments, at a second time interval referred to herein as a section 169 of graph 100, pump 44 flows (e.g., to catheter 21) at a given time, volume of fluid 88 similar to the volume flown by pump 44 if piston 99 were moved at the BLS speed, as described for section 174 above.

In some embodiments, controller 33 is configured, in response to a signal received from processor 39, to move piston 99 within cylinder 111 in a periodic cycle that alternately reverses the direction of movement of piston 99, so as to pump fluid 88 through inlet-outlet ports 112 and 114. When physician 30 decides to stop irrigating tissue of heart 26, or when system 20 stops the irrigation automatically, processor 39 sends a signal to controller 33 to stop moving piston 99 within cylinder 111, and the irrigation stops.

Figure 4:
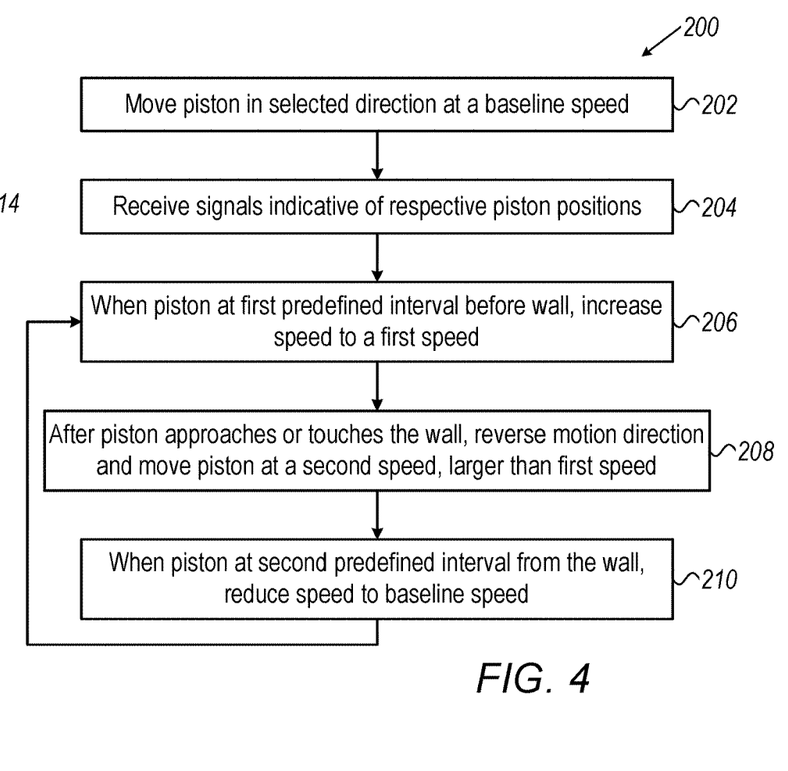
FIG. 4 is a flow chart that schematically illustrates a method for flowing a constant output of irrigation fluid over time, in accordance with an embodiment of the present invention.

FIG. 4 is a flow chart 200 that schematically illustrates a method for flowing a constant output of irrigation fluid 88 by pump 44, in accordance with an embodiment of the present invention. The method begins at a piston movement step 202 with controller 33 receives a control signal from processor 39 to irrigate tissue of heart 26 with irrigation fluid 88, and controlling the movement of piston 99 in selected direction at baseline speed (BLS), as described in interval 164 of FIG. 3B above.

At a position signal receiving step 204, controller 33 receives from PPSA 54 signals indicative of the respective positions of piston 99 moved toward wall 77, as described in FIG. 3B above. At a first speed setting step 206, in response to receiving from PPSA 54 a signal indicating that piston concluded the travel in interval 164, controller 33 controls the movement of piston 99 toward wall 77 at speed S1 along interval 165. Subsequently, when approaching wall 77, controller 33 reduces the speed of piston 99 to a complete stop when reaching wall 77, as described in FIG. 3B above.

At a second speed setting step 208, in response to receiving from PPSA 54 a signal indicating that piston makes contact with or approaching (e.g., within the aforementioned predetermined interval from) wall 77, controller 33 reverses the moving direction and controls the movement of piston 99 toward wall 66 at speed S2 along interval 167, as described in FIG. 3B above. At a third speed setting step 210, in response to receiving from PPSA 54 a signal indicating that piston concluded the travel in interval 167, controller 33 sets the movements of piston 99 toward wall 66 at BLS along interval 179, as described in FIG. 3B above. In some embodiments, step 210 is typically concluded when controller 33 receives from PPSA 54 a signal indicating that piston concluded the travel in interval 179, and the method loops back to step 206 and continues until controller 33 receives from processor 39 a control signal to stop irrigating tissue of heart 26.

Controlling Irrigation Pump Between and During Ablation

Figure 5:
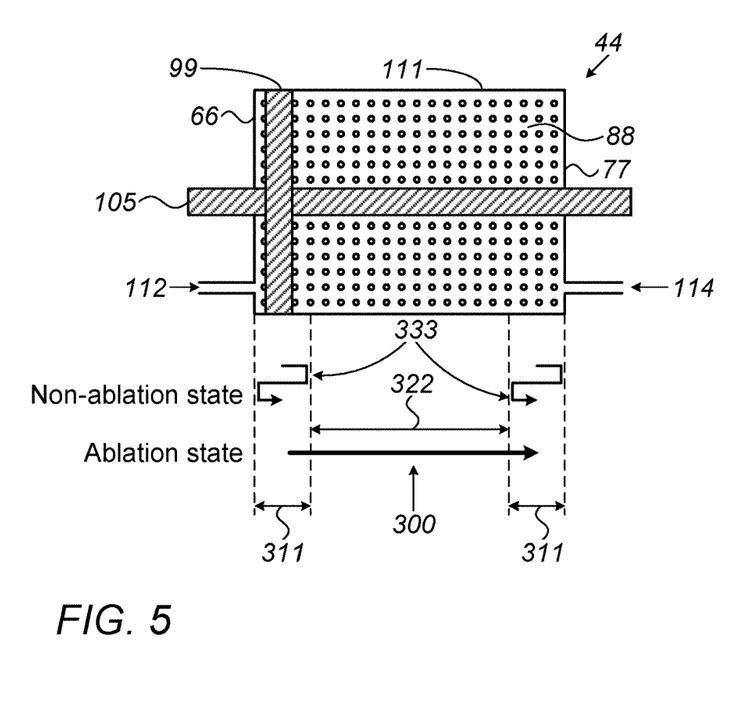
FIG. 5 is a schematic, pictorial illustration of a movement profile of a piston in a dual-action irrigation pump used in a cardiac ablation procedure, in accordance with another embodiment of the present invention.

FIG. 5 is a schematic, pictorial illustration of a movement profile of piston 99 in pump 44 used in a cardiac ablation procedure, in accordance with another embodiment of the present invention. In some embodiments, controller 33 is configured to operate pump 44 in two operational modes, referred to herein as first and second operational modes.

In some embodiments, the first operational mode is carried out at a predefined interval 311 that does not exceed a predefined distance, such as but not limited to about 0.5 cm from wall 66 or 77. At the first operational mode, controller 33 is configured to operate pump 44 at a non-ablation state 333, such that distal end 22 is operated by physician 30 in heart 26, but is not ablating tissue of heart 26. Note that in an ablation state that will be described in detail below, it is important to pump fluid 88 without changing the movement direction of piston 99, therefore, non-ablation state 333 is used by controller 33 for positioning piston 99 in close proximity to one of walls 66 and 77, and if needed to carry out a specified irrigation within heart 26 as described in detail below.

In some embodiments, in non-ablation state 333, controller 33 is configured to control piston 99 to oscillate over predefined interval 311. In such embodiments, piston 99 is moved within interval 311 in a periodic cycle that alternately reverses the direction of movement of piston 99, so as to pump fluid 88 through inlet-outlet ports 112 and 114. Note that by oscillating piston 99 within interval 311, irrigation assembly 11 irrigates tissue of heart 26 with pulses of fluid 88, defined by the width of interval 311 and by the movement speed of piston 99, or in other words, by the cycle time of one oscillation, e.g., starting and finishing at wall 66.

In other embodiments, controller 33 may control the movement of piston 99 within interval 311 to pump a constant flow of fluid 88, for example, by applying the technique described in FIGS. 3B and 4 above.

In alternative embodiments, controller 33 may control the movement of piston 99 using any other suitable movement profile. For example, in response to instruction signals from processor 39, controller 33 may control the speed of piston 99 to change with time, so as to increase or decrease the amount of fluid 88 pumped by pump 44. This exemplary movement profile may be defined manually by physician 30, or automatically by processor 39 in response to receiving one or more signals related to the medical procedure.

In other embodiments, controller 33 may control pump 44 to stand without moving at any suitable predefined distance from wall 66 and/or 77, typically located within interval 311.

In some embodiments, controller 33 is configured to choose between operating pump 44 in an ablation state 300, typically during tissue ablation, and non-ablation 333 state, typically between ablations. In some cases, controller 33 receives an instruction signal from processor 39 to switch between states 300 and 333.

In some embodiments, in ablation state 300, which corresponds to the aforementioned second operational mode, controller 33 is configured to control piston 99 to move at a selected speed between walls 66 and 77. The selected speed may be constant during the ablation of all ablation sites in heart 26, or may vary between specific ablation sites in heart 26 in response to different ablation conditions (e.g., time, temperature and RF energy applied to tissue). Moreover, during ablation at a specific ablation site, controller 33 may change the movement speed of piston 99, for example, in response to changes in the temperature measured at the ablation site. In other words, controller 33 is configured to control piston 99 to move at a variable speed during the tissue ablation.

In some embodiments, controller 33 operates pump 44 at ablation state 300 when piston is positioned within predefined interval 322, which is out of and not overlapping with intervals 311.

In other embodiments, controller 33 may choose to switch from the first operational mode (i.e., at non-ablation state 333) to the second operational mode (i.e., at ablation state 300) when piston 99 is still situated within interval 311. Similarly, controller 33 may choose to switch back from the second operational mode to the first operational mode after piston 99 is already situated within interval 311 at the other end of cylinder 111.

In an embodiment, processor 39 may send a first instruction signal to controller 33 to switch to ablation state 300 when piston is within interval 311, in close proximity to wall 66, and a second instruction signal to switch back to non-ablation state 333 when piston is within interval 311, in close proximity to wall 77. In this example embodiment shown in FIG. 5, the arrow representing ablation state 300 starts within interval 311 situated in close proximity to wall 66, and terminates within interval 311 situated in close proximity to wall 77. In such embodiments, controller 33 is configured to operate pump 44 in ablation state 300 until piston 99 makes physical contact with wall 77.

In other embodiments, controller 33 is configured to choose between the first and second operational modes independently of processor 39. For example, in response to receiving, from PPSA 54, position signals indicating that piston 99 is situated within interval 311, controller 33 may switch from ablation state 300 of the second operational mode, to non-ablation state 333 of the first operational mode.

Additionally or alternatively, controller 33 is configured to choose between the first and second operational modes using other sequences, for example, after irrigating an ablation site of heart 26 with a predefined volume of fluid 88, or based on any other suitable signal, or by using any suitable sequence programmed in controller 33.

This particular sequence of FIG. 5 is shown by way of example, in order to illustrate certain problems, such as having sufficient fluid 88 for irrigating tissue during ablation using a dual-action pump. As described above, these problems are addressed by embodiments of the present invention that also demonstrate the application of these embodiments in enhancing the performance of a dual-action pump operating in a cardiac ablation system. Embodiments of the present invention, however, are by no means limited to these specific sorts of example pump and system, and the principles described herein may similarly be applied to other sorts of pumps and medical ablation systems.

Figure 6:
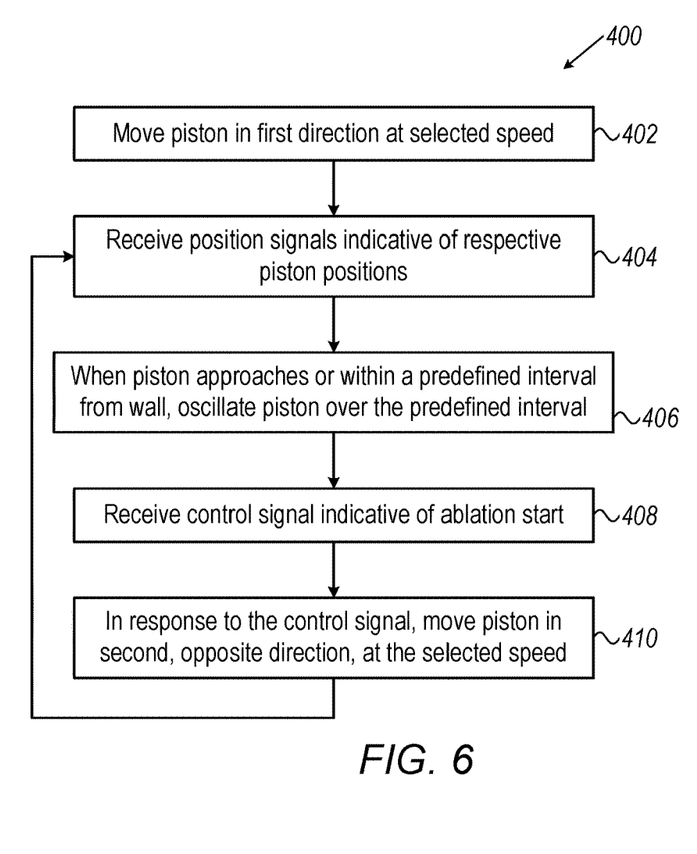
FIG. 6 is a flow chart that schematically illustrates a method for pumping irrigation fluid in a cardiac ablation procedure, in accordance with another embodiment of the present invention.

FIG. 6 is a flow chart 400 that schematically illustrates a method for pumping irrigation fluid 88 in a cardiac ablation procedure carried out by irrigation assembly 11, in accordance with another embodiment of the present invention. The method begins at a first piston movement step 402, with controller 33 controlling the move of piston 99 at a selected speed in the direction shown by the arrow of ablation state 300. Note that at step 402, controller 33 operates pump 44 in the second operational mode during the ablation of tissue in heart 26, and controls piston 99 to move toward wall 77.

At a position signal receiving step 404, controller 33 receives from PPSA 54 signals indicative of the respective positions of piston 99 moved toward wall 77, as described in FIG. 3B above. At a piston oscillating step 406, in response to receiving a position signal indicating that piston 99 is situated in close proximity to wall 77 within interval 311, controller 33 controls piston 99 to oscillate over interval 311 using non-ablation state 333, as described in FIG. 5 above.

At a control signal receiving step 408, controller 33 receives (e.g., from processor 33) a control signal indicative of starting the tissue ablation in heart 26. Note that the first irrigation depicted in step 402 is carried out when distal end 22 is positioned at a first ablation site, and the control signal of step 408 is received when distal end 22 is typically positioned at a second, different, ablation site.

At a second piston movement step 410, in response to receiving the control signal, controller 33 switches the operational mode of pump 44 and controls piston 99 to move toward wall 66 for irrigating tissue with fluid 88 during the ablation of the second ablation site. In some embodiments, controller 33 controls piston 99 to move at the speed selected at step 402 above, but in the opposite direction, i.e., toward wall 66. In other embodiments, the ablation parameters at the second ablation site may differ from the ablation parameters of the first ablation site, and therefore, the selected speed of step 410 may differ from the selected speed at step 402 above, so as to carry out suitable irrigation with fluid 88 during the ablation process at the second ablation site.

In some embodiments, after concluding step 401, the method loops back to step 404 and continues until the last ablation site has been ablated by physician 30.

Although the embodiments described herein mainly address tissue irrigation in cardiac ablation procedures, the methods and systems described herein can also be used in other applications, such as in other cardiac applications, in any type of ablation procedure applied to tissue of any other organ.

It will thus be appreciated that the embodiments described above are cited by way of example, and that the present invention is not limited to what has been particularly shown and described hereinabove. Rather, the scope of the present invention includes both combinations and sub-combinations of the various features described hereinabove, as well as variations and modifications thereof which would occur to persons skilled in the art upon reading the foregoing description and which are not disclosed in the prior art. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The invention claimed is:

1. A dual-action pump, comprising:
   (a) a cylinder comprising a first end and a second end opposite the first end, the first end including a first inlet-outlet port and the second end including a second inlet-outlet port, each of the first and second inlet-outlet ports comprising an opening in the cylinder and each of the first and second inlet-outlet ports being configured to alternately intake a fluid to the cylinder and output the fluid from the cylinder;
   (b) a piston, which is configured to be moved within the cylinder between the first end and the second end in a periodic cycle that alternately reverses a direction of movement of the piston between the first end and the second end, so as to pump the fluid through one of the first and second inlet-outlet ports; and (c) a controller, which is configured to control the movement of the piston within the cylinder between the first end and the second end so that the piston moves at each of:
  (i) a first speed in a first direction, during a first predefined interval that precedes reversing the first direction of movement to a second direction opposite the first direction,
  (ii) a second speed in the second direction, larger than the first speed, during a second predefined interval that follows reversing the first direction to the second direction, and
  (iii) a baseline speed, smaller than the first speed or the second speed, in each of the first and second directions outside the first and second predefined intervals during third and fourth predefined intervals greater than each of the first and second predefined intervals, the baseline speed being substantially the same in each of the first and second directions.

2. The pump according to claim 1, comprising a piston position sensor assembly (PPSA) that provides a control signal indicative of a position of the piston within the cylinder, the controller being configured to receive the control signal from the piston position sensor assembly, and to control the movement of the piston based on the control signal.

3. The pump according to claim 2, the controller being configured to control the movement of the piston between the first and second ends of the cylinder, the PPSA comprising:
  (a) a first electrical switch configured to produce a first position signal when the piston is situated within a predefined distance from the first end, and
  (b) a second electrical switch configured to produce a second position signal when the piston is situated within a predefined distance from the second end,
  the PPSA being configured to produce the control signal based on at least one of the first and second position signals.

4. The pump according to claim 3, the controller being configured to control a given volume of the fluid to be pumped through the first and second inlet-outlet ports during a first time interval comprising at least the first and second predefined intervals, and to control the same given volume of the fluid to be pumped through the first and second inlet-outlet ports during a second time interval that is approximately equal to the first time interval, when the piston is outside the first and second predefined intervals.

5. The pump according to claim 1, at least one of the first and second inlet-outlet ports being coupled to a fluid reservoir via a first pipe, and to a catheter via a second pipe, so as to irrigate tissue with the fluid during a medical procedure.

6. A method for pumping a fluid in a dual-action pump comprising a cylinder having a first end and a second end opposite the first end, the first end including a first inlet-outlet port and the second end including a second inlet-outlet port, each of the first and second inlet-outlet ports comprising an opening in the cylinder, and each of the first and second inlet-outlet ports configured to alternately intake a fluid to the cylinder and output the fluid from the cylinder, the method comprising:
  (a) moving a piston within the cylinder a direction of movement between the first end and the second end in a periodic cycle that alternately reverses one direction of movement of the piston to an opposite direction so as to pump the fluid through one of the first and second inlet-outlet ports; and
  (b) controlling the movement of the piston within the cylinder to each of:
    (i) a first speed, during a first predefined interval that precedes reversing the one direction of movement to the opposite direction,
    (ii) a second speed, larger than the first speed, during a second predefined interval that follows reversing the one direction to the opposite direction, and
    (iii) a baseline speed, smaller than the first speed or the second speed, in each of the first and second directions outside the first and second predefined intervals during third and fourth predefined intervals greater than each of the first and second predefined intervals, the baseline speed being substantially the same in each of the first and second directions.

7. The method according to claim 6, further comprising:
  (a) producing a control signal indicative of a position of the piston within the cylinder, and
  (b) controlling the movement of the piston based on the control signal.

8. The method according to claim 7, the act of controlling the movement of the piston within the cylinder comprising controlling the movement of the piston between the first and second ends of the cylinder, the act of producing the control signal comprising:
  (a) producing:
    (i) a first position signal when the piston is situated within a predefined distance from the first end, and
    (ii) a second position signal when the piston is situated within a predefined distance from the second end, and
  (b) producing the control signal based on at least one of the first and second position signals.

9. The method according to claim 8, the act of controlling the movement of the piston comprising:
  (a) controlling a given volume of the fluid to be pumped through the first and second inlet-outlet ports during a first time interval comprising at least the first and second predefined intervals, and
  (b) controlling the same given volume of the fluid to be pumped through the first and second inlet-outlet ports during a second time interval that is approximately equal to the first time interval, when the piston is outside the first and second predefined intervals.

10. The method according to claim 6, further comprising irrigating tissue with the fluid during a medical procedure by coupling at least one of the first and second inlet-outlet ports to a fluid reservoir via a first pipe, and to a catheter via a second pipe.

11. The pump according to claim 1, the controller being configured to:
  (i) actuate movement of the piston in the first direction at the baseline speed,
  (ii) accelerate the movement of the piston in the first direction from the baseline speed to the first speed in response to the piston reaching a first predefined distance from the second end,
  (iii) arrest the movement of the piston in the first direction in response to the piston reaching a second predefined distance from the second end, and
  (iv) actuate movement of the piston in the second direction at the second speed after arresting the movement of the piston in the first direction.

12. The pump according to claim 11, the controller being configured to decelerate the movement of the piston in the second direction from the second speed to the baseline speed in response to the piston reaching a third predefined distance from the second end.

13. The pump according to claim 12, the first and third predefined distances being the same.

14. The pump according to claim 12, the controller being configured to accelerate the movement of the piston in the second direction from the baseline speed to the first speed in response to the piston reaching a fourth predefined distance from the second end.

15. The pump according to claim 14, the controller being configured to arrest the movement of the piston in the second direction in response to the piston reaching a fifth predefined distance from the second end.

16. The pump according to claim 15, the controller being configured to actuate movement of the piston in the first direction at the second speed after arresting the movement of the piston in the second direction.

17. The pump according to claim 11, further comprising a piston position sensor assembly (PPSA) configured to provide a control signal indicative of a longitudinal position of the piston within the cylinder, the controller being configured to receive the control signal from the piston position sensor assembly.

18. The pump according to claim 17, the PPSA comprising at least one electrical switch.

19. The pump according to claim 11, the controller being configured to control a predefined volume of the fluid to be pumped through the first and second inlet-outlet ports during a first time interval between commencing accelerating the movement of the piston in the first direction and completing actuating the movement of the piston in the second direction, and to control the same predefined volume of the fluid to be pumped through the first and second inlet-outlet ports during a second time interval in which the controller actuates the movement of the piston at the baseline speed, the second time interval being approximately equal to the first time interval.

20. The pump according to claim 11, each of the first and second inlet-outlet ports being coupled to a fluid reservoir via a first conduit, and to a catheter via a second conduit, for irrigating tissue with the fluid during a medical procedure.

* * * * *